United States Patent
Lynenskhold et al.

(10) Patent No.: US 7,338,668 B2
(45) Date of Patent: Mar. 4, 2008

(54) DRUG CARRIER PELLET PRODUCTION PROCESS

(76) Inventors: Eva Lynenskhold, Standboulevarden 66, 1. tv., DK-2100 Copenhagen Ø (DK); Lone Nørgaard Jørgensen, Birkebakke 61, DK-3460 Birkerød (DK)

( * ) Notice: Subject to any disclaimer, the term of this patent is extended or adjusted under 35 U.S.C. 154(b) by 282 days.

(21) Appl. No.: 10/182,567

(22) PCT Filed: Feb. 19, 2001

(86) PCT No.: PCT/GB01/00704
§ 371 (c)(1), (2), (4) Date: Oct. 16, 2002

(87) PCT Pub. No.: WO01/60338
PCT Pub. Date: Aug. 23, 2001

(65) Prior Publication Data
US 2003/0211168 A1    Nov. 13, 2003

(30) Foreign Application Priority Data
Feb. 17, 2000 (GB) ................. 0003782.0

(51) Int. Cl.
*A61K 9/16* (2006.01)
*A01N 25/28* (2006.01)

(52) U.S. Cl. ................. 424/494; 424/421
(58) Field of Classification Search ............ 424/489, 424/490, 493–502, 417, 418, 421
See application file for complete search history.

(56) References Cited

U.S. PATENT DOCUMENTS

| | | | |
|---|---|---|---|
| 3,833,392 A * | 9/1974 | Repsher et al. | 252/301.36 |
| 4,325,739 A * | 4/1982 | Biermann et al. | 106/403 |
| 4,336,173 A | 6/1982 | Ugelstad | |
| 4,459,378 A | 7/1984 | Ugelstad | |
| 4,622,057 A * | 11/1986 | Chyung et al. | 65/17.2 |
| 5,397,576 A * | 3/1995 | Mergens et al. | 424/493 |
| 5,486,365 A * | 1/1996 | Takado et al. | 424/602 |
| 5,486,507 A * | 1/1996 | Whistler | 514/54 |
| 5,800,755 A * | 9/1998 | Withenshaw et al. | 264/117 |
| 5,830,576 A * | 11/1998 | Mehra et al. | 424/408 |
| 5,858,411 A * | 1/1999 | Nakagami et al. | 424/489 |
| 5,958,458 A * | 9/1999 | Norling et al. | 424/490 |
| 6,866,867 B2 * | 3/2005 | Staniforth et al. | 424/499 |

FOREIGN PATENT DOCUMENTS

| | | |
|---|---|---|
| EP | 0 439 373 | 7/1991 |
| EP | 1 004 296 | 5/2000 |
| WO | WO 95/34291 | 12/1995 |

OTHER PUBLICATIONS

"Application of Calcium Silicate for Medicinal Preparation. I. Solid Preparation Adsorbing an Oily Medicine to Calcium Silicate", Hiroshi Yuasa et al., 1994 Pharmaceutical Society of Japan, pp. 2327 to 2331.

* cited by examiner

*Primary Examiner*—Sharon E. Kennedy

(57) ABSTRACT

The invention provides a process for the production of drug carrier pellets comprising spray-drying a solution of a physiologically tolerable cellulosic binder containing a physiologically tolerable inert particulate carrier having a particle size D (v, 0.5) of less than 50 μm.

21 Claims, No Drawings

DRUG CARRIER PELLET PRODUCTION PROCESS

The invention relates to a process for producing pellets for use as drug carriers by spray drying and to coated spray dried pellets and pharmaceutical compositions containing such pellets.

The use of pellets as drug carriers is well established. Such pellets, optionally provided with a release-delaying coating, may be formulated into many administration forms, for example liquid suspensions or dispersions, capsules, tablets, powders etc.

Such use is described for example in WO95/34291 (Dumex) and EP-B-608850 (Recordati).

The pellets may contain the drug substance or may alternatively be coated or impregnated with the drug substance and, as mentioned above, may be provided with a release delaying coating.

Whereas coating of tablets of millimeter or larger dimensions may be achieved using traditional pan coating techniques, for small pellets (e.g. of 50 to 500 µm diameter) it is generally necessary to use fluidized bed coating techniques. Fluidized bed coating exposes the pellets to relatively severe shear forces and if the pellets are insufficiently robust they show a tendency to fracture and as a result it is difficult to obtain the desired drug release profile or indeed to calculate the amount of coating material needed.

For this reason, spray drying, which is a simple and economical technique for producing pellets, has generally been considered inappropriate for producing pellets for coating by fluidized bed techniques since spray dried pellets are normally hollow and relatively fragile.

In WO95/34291 it was described how pellets capable of being coated using a fluidized bed technique could be produced if the mixture being spray-dried contained a binder and an inert particulate carrier material, for example a calcium salt such as calcium carbonate or a calcium phosphate. The spray-dried pellets described in WO95/34291 however are still relatively fragile and there still exists a need for spray-dried pellets which are more robust.

We have now surprisingly found that pellet robustness may be improved if a cellulosic binder is used in the liquid which is spray-dried.

Thus viewed from one aspect the invention provides a process for the production of drug carrier pellets comprising spray-drying a solution of a physiologically tolerable cellulosic binder containing a physiologically tolerable inert particulate carrier having a particle size D(v, 0.5) of less than 50 µm.

Viewed from a further aspect the invention provides spray-dried pellets comprising a physiologically tolerable cellulosic binder and a physiologically tolerable inert particulate carrier having a particle size D(v, 0.5) of less than 50 µm.

Viewed from a still further aspect the invention provides a pharmaceutical composition comprising spray-dried pellets according to the invention containing, impregnated with or coated with an active drug substance, said composition optionally further comprising at least one pharmaceutically acceptable carrier or excipient.

D(v, x) is a measure of particle size meaning that 100x % of the particles by volume have a size below the specified value. Thus a D(v, 0.5) value of 50 µm means that the mean particle size by volume is 50 µm. D(v, x) values may be determined at pressures of 0.25 to 2.5 bar using a Malvern Mastersizer from Malvern Instrument Ltd., United Kingdom. Unless otherwise specified D(v, x) values referred to herein are as determined under atmospheric pressure (1 bar).

D(v, x) values may also be used to provide an indication of the dispersity (variation in particle size) of a particulate. One such indication is referred to as the "span" and is calculated as (D(v, 0.9)–D(v, 0.1))/D(v, 0.5).

The particle size of the inert particulate carrier is desirably as small as possible as in this way the sphericality of the resultant spray-dried pellets is improved. Desirably therefore the inert particulate has a mean particle size (by volume) of less than 40 µm, more preferably less than 20 µm and still more preferably less than 10 µm. Nanoparticulate carriers, e.g. having mean particle size of as small as 5 nm, may be used, but generally the particulate will have a mean particle size of at least 100 nm, more generally at least 500 nm and still more preferably at least 1 µm. The span of the inert particulate carrier used according to the invention is desirably as small as possible in order to optimize the uniformity of packing of the particles within the spray dried pellets. The span of a particulate material may be reduced by screening to remove over- or under-sized particles, or alternatively the particles may be made by a process which inherently yields a low span value, e.g. a process as described in U.S. Pat. No. 4,336,173 or U.S. Pat. No. 4,459,378.

The spray-dried pellets produced by the process of the invention desirably have a D(v, 0.5) of 25 to 500 µm. Smaller pellets are difficult to coat using fluidized bed techniques and larger pellets are difficult to produce by spray-drying. Preferably the pellets have a D(v, 0.5) of 60 to 400 µm, more preferably 80 to 300 µm. Particularly preferably at least 80% by volume of the spray-dried pellets are between 50 and 500 µm in size.

While spray-drying generally produces pellets having a relatively narrow size distribution, it will often be desirable to screen the spray-dried pellets to remove under-sized and/or oversized pellets, i.e. to reduce the "span" value. Normally no more than about 5% wt. of pellets need to be removed to produce a desirable span value. Generally the span value of the pellets which are to be coated will desirably be no greater than 2.5, preferably no greater than 1.5, more preferably no greater than 1, especially preferably no greater than 0.8 (determined at 0.5 bar). A low span value is desirable as it is then possible to calculate more accurately the amount of coating material required to give the pellets the desired loading of drug material and/or the desired drug release profile.

The inert particulate carrier used in the process of the invention may be any physiologically tolerable organic or inorganic material, and may be water-insoluble or water-soluble, for example a polymer, carbon (e.g. activated carbon), a clay (e.g. kaolin) or an inorganic carbonate, silicate, sulphate, phosphate or oxide, for example calcium carbonate, calcium silicate, calcium magnesium silicate, calcium lactate, calcium gluconate, calcium glycerophosphate, calcium phosphates, calcium hydrogen phosphate (e.g. in tribasic, dibasic or monobasic forms, i.e. $Ca_3(PO_4)_2$, $CaHPO_4.2H_2O$ and $Ca(HPO_4)_2.H_2O$), calcium glucuronate, calcium aspartate, calcium glucoheptonate, sodium hydrogen carbonate, sodium sulphate, magnesium sulphate, magnesium carbonate, barium carbonate, barium sulphate, or hydroxy apatites. Inorganic materials, and in particular calcium carbonate and especially calcium hydrogen phosphate (e.g. its various hydrates and anhydrous calcium hydrogen phosphate), are especially preferred. In the case of calcium carbonate, it is preferred that this be in the calcite form.

Where the spray dried pellets are to be further processed with an aqueous medium, e.g. where they are to be coated using an aqueous coating composition, the inert carrier material will preferably be water-insoluble or at least very poorly water-soluble. However if further processing of the spray dried pellets does not involve contact with an aqueous medium water soluble inert carrier materials may be acceptable. In general however water-insoluble or very poorly water soluble inert carrier materials, e.g. having a solubility in water at pH 7 and 21° C. of less than 0.1 g/mL, will be preferred.

The inert particulate carrier preferably has a true density of 1.5 to 5 g/mL, especially 2 to 3 g/mL. This may however correspond to a bulk (i.e. loose) density of 0.1 to 1.4 g/mL, for example 0.7 to 1.4 g/mL, especially 0.2 to 1.0 g/mL, for example 0.7 to 1.0 g/mL, more especially 0.2 to 0.9 g/mL, for example 0.7 to 0.9 g/mL. The tapped density is desirably in the range 0.8 to 1.6 g/mL, especially 0.9 to 1.55 g/mL and more especially 0.91 to 1.5 g/mL. Examples of particularly suitable inert carriers include calcium carbonate Microstevns (available from Faxe & Kalk, Denmark), calcium carbonate (available from Nomeco, Denmark), Merck 2064 (available from Merck, Germany), Scoralite 1A and 1B (available from Scora Watrigent SA, (France), and Pharmacarb LL (available from Crompton & Knowles, USA) and anhydrous calcium hydrogen phosphate Di-Cafos (available from Budenheim, Germany).

The density and relative quantity of inert particulate carrier used is preferably selected such that the spray dried pellets have a true density of at least 1.7 g/mL, more preferably at least 1.8 g/mL, still more preferably at least 1.9 g/mL, especially at least 2.0 g/mL, more especially at least 2.1 g/mL, particularly at least 2.2 g/mL, e.g. up to 2.7 g/mL. Alternatively stated, the spray dried pellets preferably have a particle density of at least 1.3 g/mL, more preferably at least 1.45 g/mL, especially at least 1.5 g/mL, more especially at least 1.55 g/mL, particularly at least 1.6 g/mL, more particularly at least 1.7 g/mL, e.g. up to 1.9 g/mL.

The term "true density" as used herein in relation to a particulate means the ratio between mass of the particles and their actual volume. The term particle density as used herein has its conventional meaning and can be measured by mercury displacement. Both terms are defined in "Physical Characterization of Pharmaceutical Solids", volume 70, pages 272-273, Britain (Ed.), Marcel Dekker Inc [1995].

The inert particulate carrier material will preferably constitute from 2 to 99.5% wt of the spray-dried pellets, for example 2 to 99%, alternatively from 15 to 99.5%, for example 15 to 99%, still more preferably 30 to 98% wt. especially 40 to 97.5% wt, more especially 50 to 97% wt, in particular 60 to 97% wt, more particularly 80 to 97% wt, still more preferably 89 to 96.5% wt.

The cellulosic binder used in the process of the invention may be any cellulose or cellulose derivative, e.g. ester or ether, which is at least partly soluble in the solvent or solvent system used for spray drying, which is physiologically tolerable and which is capable of acting as a binder. Examples include alkyl celluloses (e.g. $C_{1-3}$ alkyl celluloses such as methylcellulose and ethylcellulose), hydroxyalkylalkyl celluloses (e.g. hydroxy $C_{1-5}$ alkyl $C_{1-5}$ alkyl celluloses such as hydroxypropylmethylcellulose and hydroxyethylmethyl-cellulose), hydroxyalkylcelluloses (e.g. hydroxypropylcellulose) and carboxyalkyl celluloses (e.g. carboxy $C_{1-5}$ alkyl celluloses such as sodium carboxy methyl cellulose). Such cellulosic binders are available commercially, e.g. as powdered cellulose (available from Edward Mendell Co., Inc.), cellulose acetate phthalate (available from FMC as Aquasteric®), Methocels (from Colorcon), Avicels (from Edward Mendell Co., Inc.), Pharmacoats (from Shin Etsu, Japan), Benecels (available from Dow Chemical), Culminals (available from Dow Chemical), and Walocels. (See also "Handbook of Pharmaceutical Excipients", 2nd Edition, the Pharmaceutical Press, 1994.

The cellulosic binders are preferably hydroxyalkyl-alkyl celluloses, especially hydroxypropylmethyl celluloses, e.g. Pharmacoat 603 from Shin Etsu or Methocel K100 available from Colorcon and Dow Chemical.

The cellulosic binders preferably have a weight average molecular weight of 10 to 100 kD, especially 15 to 80 kD and viscosities of 2 to 6 mPa.s in 2% wt. aqueous solution at 21° C.

The cellulosic binder preferably constitutes from 0.5 to 15% wt (dry solids basis) of the spray-dried pellets, more preferably 1 to 10% wt, still more preferably 2 to 6% wt, especially 3 to 5% wt, in particular 3 to 4.5% wt. Where the binder content is too high, the pellets have a tendency to agglomerate.

The spray-dried pellets produced according to the invention may if desired contain further components besides the inert particulate carrier and the cellulosic binder, for example active drug substances, diluents or fillers, antifoaming agents, sweeteners, anti-oxidants, buffers, suspending agents, anti-microbial preservatives, disintegrants, coloring agents, plasticizers, desiccants, acidifying agents, surfactants, wetting agents, humectants and emulsifiers. Such additional components will preferably constitute 0.1 to 80% wt (dry solids basis) of the spray-dried pellets, more preferably 0.5 to 25% wt, still more preferbly 1 to 20% wt, especially 2 to 10% wt, more especially 2 to 8% wt, in particular 3 to 6% wt.

Examples of physiologically tolerable diluents, fillers and sweeteners include sugar alcohols, mono, di and oligosaccharides and derivatives thereof (e.g. sucrose, fructose, lactose, maltodextrin, insulin, fructooligosaccharides, mannitol, sorbitol, xylitol, inositol and isomalt) and artificial sweeteners (e.g. acesulfam and aspartame).

Particularly preferred fillers include lactose (e.g. lactose monohydrate) and maltodextrin. Such fillers most preferably constitute no more than 25% wt (dry solids basis) of the spray-dried pellets, especially 2 to 10% wt, more especially 3 to 8% wt.

Antifoaming agents are preferably used in the spray drying process and as a result if this is done small quantities will be present in the spray-dried pellets, e.g. up to 1% wt (dry solids basis). Examples of physiologically tolerable antifoaming agents include silicone oil (e.g. SE2 from Bie & Berntsen, Denmark) and Antifoam M10 (from Dow Corning, USA).

Where an active drug substance is incorporated within the spray-dried pellets, it may be a water soluble or water insoluble drug substance. In the latter case, the drug substance is preferably in microcrystalline or amorphous form with a particle size comparable to or smaller than the particle size of the inert particulate carrier material. The drug substance if present in the liquid to be spray-dried may constitute a major or more preferably aminor proportion of the spray-dried pellets (on a dry solids basis (DSB)). Thus for example the drug substance may constitute up to 80% wt DSB, conveniently up to 50% wt DSB, preferably up to 25% wt DSB, e.g. 0.5 to 20% wt DSB, more preferably 1 to 10% wt DSB of the spray-dried tablets. Further drug substance may be added by coating the spray-dried pellets.

In general, the liquid to be spray-dried may be prepared by dissolving the cellulosic binder in heated solvent (e.g.

water), cooling to ambient temperature and adding the remaining components. The overall dispersion may be introduced into the spray-drying apparatus at ambient, or if desired, elevated temperature.

Spray drying in the process of the invention may be effected in a conventional manner using conventional equipment, e.g. as available from Niro A/S, Denmark. A dispersion of-the components of the spray dried pellets in a physiologically tolerable solvent or solvent mixture (e.g. water, water/alkanol, water/ether, etc.) may be sprayed under pressure, and preferably upwards, into a drying chamber. The dispersion will generally contain about 30 to 70% wt solvent, preferably 40 to 50% wt solvent, and preferably also 0.03 to 1% wt antifoaming agent, particular 0.08 to 0.2% wt. The inlet temperature is preferably at least 100° C., especially at least 200° C., e.g. up to 350° C. The pellets are preferably dried to a residual moisture content of no more than 1% wt, more preferably no more than 0.7% wt (determined as weight loss on drying for 10 minutes at 105° C.)

The robustness of the spray-dried pellets, in other words their suitability for subsequent fluidized bed coating, can be measured by a so-called "Malvern Robustness Test". In this, D(v, 0.5) of a sample of uncoated spray-dried pellets is determined at 0.5 and 1.5 bar, i.e. below and above atmospheric pressure, and a robustness value Rv is determined as $$Rv = \frac{100(D(v, 0.5)_{0.5 bar} - D(v, 0.5)_{1.5 bar})}{(D(v, 0.5)_{0.5 bar})}$$

In the sample tested, $D(v, 0.5)_{0.5\ bar}$ should be no more than 250 μm and $D(v, 0.1)_{0.5\ bar}$ should be no lower than 20 μm. Preferably $D(v, 0.5)_{0.5\ bar}$ should be no more than 225 μm, more preferably no more than 200 μm, especially no more than 180 μm. Particularly preferably $D(v, 0.5)_{0.5\ bar}$ is in the range 90 to 225 μm, more preferably 100 to 200 μm.

The Rv is preferably no more than 40, more preferably no more than 35, especially no more than 30, more especially no more than 25, particularly-no more than 20, more particularly no more than 15, most particularly no more than 10.

The Malvern Robustness Test may be used to determine the suitability of a particular spray-dried pellet composition or to determine the suitability of a particular component or component combination. In the latter case, the test composition is preferably:

| | | |
|---|---|---|
| at least 75% wt (preferably 90 to 97% wt) inert carrier | = | calcium carbonate (e.g. Mikrostevns) or more preferably calcium hydrogen phosphate (e.g. Di Cafos 92.05) or the material being tested |
| 3.5 to 6% wt (preferably 3.8% wt) binder | = | hydroxypropylmethyl cellulose (e.g. Pharmacoat 603 from Shin-Etsu) or material being tested |
| 0 to 11% wt (preferably 0 to 5% wt) inert filler or diluent | = | lactose monohydrate or maltodextrin 01982 (from Cerestar, France) or the material being tested |
| 0 to 0.2% wt antifoaming agent | = | silicon oil (e.g. SE2 from Bie & Berntsen, Denmark) or the material being tested |
| 0 to 50% wt (preferably 20% wt) | = | active drug substance if being tested |
| 0 to 10% wt | = | any other component if being tested. |

The spray-dried pellets to be tested in this way may be screened before testing to ensure that the $D(v, 0.5)_{0.5\ bar}$ and $D(v, 0.1)_{0.5}$ bar values are within the specified limits.

While the Malvern Robustness Test may be seen primarily as a means of testing whether particular components or combinations of components are satisfactory, the spray-dried pellets produced used according to the invention preferbly also have Rv values below the limits listed above.

The spray-dried pellets of the invention are particularly suited for use as drug carriers since their robustness makes them suitable for coating with drug substances and their relatively smooth, non-porous and spherical form and uniform sizes makes it easier to load with the desired drug dosage and so provide the desired drug release profile.

While the spray-dried pellets produced by the process of the invention may be used as they are, e.g. as a powder, by filling into capsules, compressing into tablets or dispersion in a matrix, for example a gel, it is especially preferred that they first be coated with one or more coatings and/or impregnated with an active drug substance. To this end, conventional pellet coating techniques may be used; however especially preferably the pellets are coated or impregnated using a fluid bed coating technique. In this regard conventional fluid bed coating apparatus, such as that available from Glatt GmbH, Germany, and in particular a fluid bed with a Wurster insert, may be used. (The Wurster involves the use of a spray nozzle at the base of the bed which causes the particles to circulate within the fluid bed).

It is however preferred that before being coated or impregnated the spray dried pellets of the invention are first screened to remove fines and possibly also oversized pellets.

The spray dried pellets are preferably first coated or impregnated with a coating liquid comprising in dispersion or more preferably in solution at least one active drug substance. Thereafter, if desired, the pellets may be further coated, for example with one or more coatings such as sugar coatings, bioadhesive coatings, film coatings or release modifying coatings (e.g. release delaying or gastric juice resistant coatings).

The coating of the spray-dried pellets with an active drug substance may of course be effected simultaneously with coating with other materials, e.g. binders, sugar coatings, release modifying coatings, bioadhesive coatings, film coatings, etc. Generally, however, where a sugar coating, release modifying coating, bioadhesive coating etc. is desired this will be applied after the spray-dried pellets have been coated with or impregnated with an active drug substance.

Thus for example a water-soluble drug substance may be coated onto the spray-dried pellets using a GPCG I Glatt fluid bed with Wurster using an inlet temperature of about 60° C., a product temperature of about 34° C. and a spray rate of about 10 g/min. Likewise a water-insoluble drug substance may be coated onto the pellets in the same apparatus using an inlet temperature of about 55° C., a product temperature of about 28-29° C. and a spray rate of about 12.5 g/min. Similarly a polymeric film (e.g. of Surelease E-7-7050) may be provided on the pellets using the same apparatus using an inlet temperature of about 60° C., a product temperature of about 30-31° C. and a spray rate of about 9 g/min.

The active drug substance coated onto or impregnated into the spray-dried pellets or incorporated in the pellets during their production may be any active drug substance capable of delivery in pellet-supported form. Examples of such drug substances are listed in WO95/34291 and include peptides, proteins, vaccines, nucleic acids (e.g. DNA), analgesics (e.g. buprenorphine), antiinflammatories (e.g. ibuprofen), tranquilizers (e.g. diazepam), cardiac glycosides (e.g. digoxin), narcotic antagonists (e.g. naloxone), anti parkinsonism agents (e.g. bromocriptine), antidepressants (e.g. imipramine), antineoplastic agents and immunosuppressants (e.g. bleomycin), antivirals (e.g. acyclovir), antibiotics (e.g. erythromycin), antifungals (e.g. ketoconazole), antimicrobials (e.g. tetracyclins), appetite suppressants (e.g. fenfluramine), antiemetics (e.g. metoclopramide), antihistamines (e.g. chlorpheniramine), antimigraines (e.g. dihydroergotamine), vasodilators (e.g. nifedipine), antianginals (e.g. glyceryl nitrate), calcium channel blockers (e.g. verapamil), hormonal agents (e.g. estradiol), contraceptives (e.g. norgestrel), antithrombotics (e.g. warfarin), diuretics (e.g. flunarizine), antihypertensives (e.g. propanolol), anaesthetics (e.g. lidocaine), dependency drugs (e.g. methadone), corticosteroids (e.g. betamethasone), vitamins, dermatological agents (e.g. nitrofurantoin), opthalmic agents (e.g. pilocarpine), steroids (e.g. progesterone), azoles (e.g. imidazoles), nitro compounds (e.g. nitroglycerine), amines (e.g. benzocaine), oxicams (e.g. piroxicam), mucopolysaccharides (e.g. thiomucase), opioids (e.g. morphinie), prostaglandins (e.g. PGA, PGB, PGE or PGF, for example enaprostil), benzamides (e.g. metoclopramide), peptides (e.g. growth factors, interferons, insulin, SOD, urokinase, EPO, etc), xanthines (e.g. theophylline), catecholamines (e.g. salbutamol), dihydropyridines, contrast agents, thiazides (e.g. hydrochlorothiazide), sydnonimines (e.g. molsidomine), oligosaccharides, and polysaccharides, e.g. glycosaminogylcans, e.g. sulphated polysaccharides (e.g. heparin and heparinoids).

It will be appreciated that the term active drug substance is used to denote any substance having a desired effect (e.g. a therapeutic, diagnostic, prophylactic, supportive or terminal effect) on the end user and thus encompasses biologically or pharmacologically active substances, antigens, etc. as well as other substances which have utility in the treatment or prevention of diseases, ailments or conditions of the human or animal body, or in the regulation of a physiological condition or which have effects on viruses, living cells or organisms.

The active drug substance is particularly suitably one which should be administered in relatively accurate or relatively small dosages or one which should desirably have a relatively accurate release profile over time. For such drugs, administration on a particulate support, optionally provided with a release modifying coating, is particularly effective.

The quantity of active drug substance used per dosage unit will of course depend on the species, sex, age, condition and size of the subject being treated, the nature and severity of the condition being treated, the potency or efficiency of the drug substance, and the intended mode of administration. For each drug substance the dosage used can thus be a conventional dosage or a dosage determined in a conventional fashion. In general however the dosage per spray-dried pellet will normally fall in the range of 0.1 to 90% wt relative to the weight of the uncoated pellet (excluding any drug substance in the uncoated pellet), preferably 1 to 80% wt, more preferably 5 to 60% wt, especially 10 to 55% wt.

The active drug substance will generally be applied to the spray-dried pellets in the form of a solution or dispersion in a physiologically tolerable solvent or solvent mixture, optionally incorporating other components such as binders (e.g. polyvinylpyrrolidone), sweeteners, pH modifiers, anti-oxidants, etc.

Any further coating will generally be to provide the desired release profile for the active drug substance, to mask the taste of the active drug substance (e.g. where noscapine or theophylline is used), or to provide desired bioadhesion. In some cases two or more such coatings may be applied, e.g. a release modifying coating followed by a bioadhesive coating. The overall coating or set of coatings can thus be designed to release the active drug substance immediately upon administration or alternatively at or over a desired time period following administration or at a desired location within the patient's body (see for example WO95/34291).

Suitable coatings include for example:

film coatings of cellulose derivatives (e.g. hydroxypropylmethylcellulose, ethyl cellulose, methyl cellulose, hydroxyethylmethylcellulose, hydroxypropylcellulose and carboxymethylcellulose), acrylic or metacrylic polymers (e.g. Eudragit, available from Röhm GmbH, Germany), polyvinylpyrrolidone and polyethylene glycol;

sugar (or sugar substitute) coatings;

bioadhesive coatings (e.g. fatty acid esters such as glyceryl monooleate); and release modifying coatings such as for example methacrylic polymers, cellulose acetate phthalate, bees wax shellac, etc).

Such coatings may include further components such as plasticizers, antiadhesives, colors, etc. and may be applied as a solution or suspension in a physiologically tolerable solvent or solvent mixture.

For coating or impregnating the spray-dried pellets, the use of aqueous solutions or dispersions is preferred but organic solvents such as alkanols (e.g. ethanol, methanol, propanol and isopropanol), ketones (such as acetone or toluene), and esters (such as ethyl acetate) may also be used. Chlorinated hydrocarbons (such as methylene chloride) may be used but are generally not preferred.

For subsequent coatings, in particular non-fludizied bed coating techniques (e.g. pan-coating, spray drying, electrostatic coating, etc.) may be used if desired. However fluidized bed coating is still preferred.

The amount of any coating applied to the spray-dried pellets depends on the size of the pellets and the desired effect of the coating, e.g. the desired release pattern.

As mentioned above, the spray-dried pellets (especially where they incorporate an active drug substance) may be used without any coating taking place. The coated or uncoated pellets may be used as powders or may be formulated into other pharmaceutical dosage forms using conventional pharmaceutical materials and additives, e.g. dispersion media, binders, pH modifiers, capsule hulls, sweeteners, anti-oxidants, gums, lubricants, etc. Examples of suitable administration forms includes tablets, coated tablets, capsules, dispersions, suspensions, syrups, suppositories, sprays, patches, gels, creams, ointments, pastes, etc. These can be produced by conventional means.

Tablets, coated tablets and capsules are preferred administration forms for the spray-dried optionally coated pellets.

All patents, patent applications and other publications referred to herein are hereby incorporated by reference.

The invention will now be described further with reference to the following non-limiting Examples:

Materials

Materials employed in the Examples below are given in the following. The following abbreviations are used:

| Ph. Eur.: | European Pharmacopoeia |
|---|---|
| USP: | United States Pharmacopoeia |

Inert Carrier Material

Anhydrous dibasic calcium hydrogen phosphate (anhydrous calcium hydrogen phosphate, $CaHPO_4$) was obtained from Budenheim, Germany (Di-cafos, anhydrous, fine powder, C52-05/C92-05).

Calcium carbonate ($CaCO_3$) was obtained from Faxe Kalk, Denmark (Faxe Kalk Mikrostevns).

| $CaHPO_4$: | |
|---|---|
| Bulk/tapped density: | 0.74/1.47 g/ml |
| Sedimentation volume: | 118 and 120 mm (mean: 119 mm) before settling, 49 and 61 mm (mean: 55 mm) after settling |
| Particle shape: | cubic, non porous, agglomerated |
| Total surface area (BET): | 1.17-3.06 m$^2$/g |
| Mean volume diameter measured at 0.5 bar (D(v, 0.5)$_{0.5\ bar}$): | 8.92 μm |
| $CaCO_3$: | |
| Suppliers data: | Diameter 2.3 μm 100% calcite crystals Porosity 40-50% Total surface area (BET) 2.2 m$^2$/g Density 2.7 g/cm$^3$ |
| Bulk/tapped density: | 0.40/0.91 g/ml |
| Sedimentation volume: | 117 mm before settling, 112 mm after settling |
| Particle shape: | round, cubic, non porous |
| Total surface area (BET): | 2.1 m$^2$/g |
| Mean volume diameter measured at 0.5 bar (D(v, 0.5)$_{0.5\ bar}$): | 2.7 μm |
| Active drug substances | |
| Diltiazem hydrochloride: | |
| Solubility: | >100 mg/ml water |
| Pharmacopoeia grade, supplied by Profarmaco S.r.l., Italy. | |
| Furosemide: | |
| Solubility: | <0.1 mg/ml water |
| Particle size: | <10 μm |
| Pharmacopoeia grade, supplied by FIS, Italy. | |

Fillers

Lactose monohydrate, supplied by Meggle, Germany.

Maltodextrin 01982, supplied by Cerestar, France.

Binders

Hydroxypropylmethylcellulose (HPMC), from Shin Etsu, Japan (Pharmacoat 603).

Polyvinylpyrrolidone PVP 29-32, such as PVP K30, supplied by Unikem, Denmark.

Anti-Foaming Agent

Antifoam M10, supplied by Dow Corning, USA.

Silicone oil antifoam SE 2, obtained from Bie & Berntsen, Denmark.

Coating Material

Surelease® E 7-7050, obtained from Colorcon Ltd, United Kingdom. Surelease® is an aqueous polymeric dispersion having the following composition:

| Polymer: | ethylcellulose |
|---|---|
| Plasticizer: | DBS (dibutylsebacate) |
| Stabiliser: | oleic acid |
| Anti-adherent: | fumed silica |
| Aqueous base: | ammonium hydroxide solution |
| Total solid content: | 25% w/w |

Solvent/Carrier

Water was employed in the form of distilled or otherwise purified water.

Apparatus and Methods

Spray Drying Equipment

Two spray dryers (having different dimensions) were employed:

NIRO SD-6.3N spray drying equipment: The spray drier had a diameter of 2.0 m, a cylindrical height of 2.0 m and a 60° cone. A mono-pump for the pressure nozzle atomiser was placed at the bottom of the chamber with the spray pointing upwards.

NIRO S 12.5 spray drying equipment: The spray drier had a diameter of 2.55 m, a cylindrical height of 2.95 m and a 60° cone. A mono-pump for the pressure nozzle atomiser was placed at the bottom of the chamber with the spray pointing upwards.

Coating Equipment

A fluidised bed GPCG I/6" Wurster supplied by Glatt GmbH, Germany was employed.

Sedimentation Volume

A sample of 10 g was suspended in 20 ml of water (aqua purificata) in a glass tube (total volume: 35 ml; diameter: 18 mm). The sample was shaken manually and then placed in a rotamixer rotating at 20 rpm for 20 min. The sample was then allowed to sediment for 60 minutes after which the height of the sediment was measured.

Particle Shape

The shape of particles was observed by microscopy. Visual inspection was also used for evaluation of the appearance of the surface of particles and of any agglomeration of the particles. Visual inspection may also be employed to observe a balloon effect, i.e. whether the cores contain air-filled hollow spaces.

Scanning Electron Microscopy (SEM)

A scanning electron microscope of the type LEO 440 was used for this purpose. A secondary electron detector was used for determination of the 3-dimentional topography of the pellets. Samples were prepared by cross-section of the pellets with a scalpel to obtain a uniform breaking zone. The samples were glued to an aluminium platform with carbon glue and sprayed with approx. 20 nm of carbon and gold. Digital pictures were obtained and the uniformity and appearance of the coated layer and surface of the pellets were evaluated Measurement of Mean Volume Diameter—the "Malvern Size Test"

A Malvern Mastersizer from Malvern Instruments Ltd, United Kingdom, was employed. Measurements of the mean volume diameter, D(v, 0.5), as well as particle size distribution were carried out by introducing the pellets through a nozzle (at a pressure of 0.5 bar) perpendicular to the laser beam of the equipment. The measurements were performed with a 300 mm lens and a beam length of 10 mm. In order to calculate the mean volume diameter, D(v, 0.5), a polydisperse analysis model was employed. The analysis techique used fits a single curve to the particle size distribution and thus may exclude fines or over-sized particles. Generally less than 5% vol of the particles are excluded in this way.

Measurement of Robustness of Pellets—the "Malvern Robustness Test"

Measurements of the mean volume diameter, D(v, 0.5) at pressures of 0.5 bar and 1.5 bar were carried out as described above in connection with the "Malvern Size Test". The robustness of the pellets was expressed as a robustness value (Rv) as discussed above.

A low "robustness-value" indicates that the pellets are indeed robust, whereas a high "robustness-value" indicates that the pellets are friable and tend to break when the pressure is increased.

Total Surface Area Measured by the BET-method (Raw Materials Only)

The measurements were performed on a Coulter SA 3100 using the so-called BET model. A sample of about 1 g is de-gassed at 60° C. for 4 hours before measuring the total surface area.

Bulk and Tapped Density

Bulk and tapped densities were measured by use of an apparatus obtained from J. Engelsmann AG, Apparatgebau, Ludvigshafen a. Rh., Germany in accordance with Ph. Eur. 3rd Ed. 2.9.15.

True Density

The true density was measured by use of a Micromeritics Accupyc 1350 apparatus employing research grade helium as inert gas. The sample was weighed in a chamber insert of 10 ml. A known quantity of gas was allowed to flow from the reference volume into the chamber insert containing the sample. By employing the ideal gas law the sample volume was calculated. The true density expresses the ratio between the mass of the solid particles and the actual volume thereof.

Particle Density Measured by the Mercury Displacement Method

A Pascal 140 Mercury porosimeter was employed. The mass of the pellets (determined on an analytical balance) was 0.4-1.0 g from a sieve fraction having a particle size of 125-180 μm. The sample was placed in a dilatometer, type CD 3, and outgassed. When minimum vacuum was obtained, the mercury filling operation was initiated. The volume of mercury penetrating the pores was measured directly as a function of the applied pressure; as the pressure is increased mercury enters into the smaller pores. The volume of mercury entered into the pores was measured by the change in electrical capacitance of a cylindrical coaxial capacitor formed by the dilatometer stem. The volume of mercury penetrating the pores at a pressure of 1 bar is used for calculating the particle density.

Flow Rate

The flow properties of the pellets are given as the flow rate which was measured using a glass cone. The flow rate was measured with 3 different sizes of the hole in the bottom of the cone (2.5 mm, 5.0 mm, and 8.0 mm). While blocking the hole in the bottom of the glass cone, the cone was filled to the edge with pellets. The hole was then opened and the time for the glass to be emptied was measured.

Residual Water Content

The residual water content was determined either as the loss on drying, as described below, or using a Karl Fischer titration method according to Ph.Eur. 3rd Ed, 2.5.1.

Loss on Drying

The loss on drying was determined using a Mettler balance equipped with a heating unit. The loss on drying was determined after 10 minutes at a temperature of about 105° C. The weight of the sample (after drying to a constant weight) at the start was determined as 100% and the weight of the sample after 10 minutes at about 105° C. and equilibration to room temperature was determined as 100-X % where the loss on drying was X %.

Assay

For the quantitative determination of furosemide and diltiazem.HCl in the pellets, the following HPLC-method was used:

| | |
|---|---|
| Column: | Steel, 12 cm × 4.6 mm stationary phase: Nucleosil C-1 8,5 μm |
| Mobile Phase: | Methanol:water:phosphate buffer, pH 3.5(50:45:5) |
| Flow rate: | 1.0 ml/min |
| Temperature: | Room temperature |
| Detection: | UV |
| Dissolution: | |
| Apparatus: | Paddle method, USP apparatus 2, operated at 100 rpm |
| Medium: | |
| Diltiazem.HCl: | 900 ml 0.05 M phosphate buffer solution, pH 6.8(USP) Temperature: 37 ± 0.5° C. The dissolution medium was not de-aerated before use. |
| Furosemide: | 900 ml 0.05 M phosphate buffer solution, pH 5.8(USP) Temperature: 37 ± 0.5° C. The dissolution medium was not de-aerated before use. |
| Sampling: | Samples were withdrawn after 15, 30, 45, 60, 120, 180, 240, 300, 360 min. and after 24 hours. The sample volume was replaced with fresh medium. |
| Analysis: | UV detection at absorption maximum: Diltiazem: $\lambda = 236$ nm, $A_{1\%} = 543$ Furosemide: $\lambda = 277$ nm, $A_{1\%} = 638$ |

EXAMPLE 1

Preparation of Inert Calcium Hydrogen Phosphate Cores with Maltodextrin as Filler Material A suspension was prepared from the following ingredients:

| Ingredients | kg | % w/w in suspension | % w/w dry matter |
|---|---|---|---|
| Di-cafos C 92-05 | 35.6 | 50.2 | 91.3 |
| Maltodextrin 01982 | 1.9 | 2.6 | 4.9 |
| Pharmacoat 603 | 1.5 | 2.1 | 3.8 |
| Silicone oil antifoam SE2 | ca. 0.08 | ca. 0.1 | |
| Distilled water | 31.9 | 45 | |

Preparation of Feed to Spray Dryer:

Pharmacoat 603 is dispersed in water at 90° C. The solution is cooled to 40° C. and the maltodextrin is dissolved. Then the silicon oil is added. When the foam has disappeared from the solution, the calcium hydrogen phosphate is added. If necessary more anti foam is added.

Spray Drying Parameters:

The homogeneous feed is sprayed into a NIRO S 12.5 spray dryer using a pressure nozzle atomizer positioned at the bottom of the spray chamber and with the spray pointing upwards in order to obtain as large particles as possible. The following process parameters are employed:

| | |
|---|---|
| Inlet temperature: | about 270-290° C. |
| Outlet temperature: | about 122° C. |
| Fluidising air velocity: | 1260 kg/hour |
| Flow rate of feed: | 88-95 l/h |
| Nozzle pressure: | about 20 bar |

Characterisation of Spray Dried Pellets:

Six batches were prepared as described above and the mean results are shown in Table 1 below. Examination of the pellets performed by SEM showed these to be essentially perfectly spherical pellets with a smooth surface with no pores.

A blend of the batches produced was made and determined to have the following characteristics:

| | | |
|---|---|---|
| Apparent density loose/tapped (g/ml): | | 0.88/1.04 |
| Malvern: | D(v, 0.5) (microns) | Span |
| 0.25 bar | 166 | 0.946 |
| 0.5 bar | 165 | 0.932 |
| 1 bar | 167 | 0.918 |
| 1.5 bar | 166 | 0.897 |
| Density (Hg) (g/ml) (sieve fraction 125-180 μm): | | 1.712 |
| True density (g/cm$^3$): | | 2.686 |
| Rv = 0 | | |

EXAMPLE 2

Preparation of Calcium Hydrogen Phosphate Pellets with Lactose as Filler Material

| Ingredients | kg | % w/w in suspension | % w/w dry matter |
|---|---|---|---|
| Di-cafos C 92-05 | 95 | 50.2 | 91.3 |
| Lactose | 5 | 2.6 | 4.8 |
| Pharmacoat 603 | 4 | 2.1 | 3.8 |
| Silicone oil antifoam SE2 | ca. 0.2 | ca. 0.1 | |
| Distilled water | 85 | 45 | |

Preparation of Feed

The feed is prepared as described in Example 1.

Spray Drying Parameters

The homogeneous feed is sprayed into a NIRO S 12.5 spray dryer using a pressure nozzle atomizer positioned at the bottom of the chamber and with the spray pointing upwards in order to obtain as large particles as possible. The following process parameters are employed:

| | |
|---|---|
| Inlet temperature: | about 280° C. |
| Outlet temperature: | about 122° C. |
| Fluidising air velocity: | 1260 kg/hour |

TABLE 1

| Loss on drying (%) | Karl Fisc. (%) | Apparent density loose/rapped (g/ml) | Particle size D (v, 0.5)/ span at 1.0 bar (microns) | Particle size D (v, 0.5)/ span at 1.5 bar (microns) | Difference in D (v,0.5) at 1.0 and 1.5 bar (microns) | True density (g/cm$^3$) |
|---|---|---|---|---|---|---|
| 0.51 | 0.9 | 090/0.98 | 167/0.918 | 166/0.897 | −1 | 2.686 |

| | |
|---|---|
| Feed flow: | 83 l/h |
| Nozzle pressure: | about 20 bar |

Characterisation

SEM showed perfectly spherical pellets with a smooth surface, comparable to the pellets from Example 1.

| | |
|---|---|
| Loss on drying (%): | 0.59 |
| Apparent density loose/tapped (g/ml): | 0.89/0.96 |
| Malvern: D(v, 05) (microns) | 0.25 bar: 186 |
| | 0.5 bar: 186 |
| | 1 bar: 181 |
| | 1.5 bar: 166 |
| span | 1 bar: 1.097 |
| | 1.5 bar: 1.264 |
| True density (g/cm³): | 2.652 |
| RV = 10.8 | |

EXAMPLE 3—COMPARATIVE

Preparation of calcium carbonate pellets

| Ingredients | kg | % w/w in suspension | % w/w dry matter |
|---|---|---|---|
| Calcium carbonate | 36.5 | 36.5 | 96 |
| PVP 30 | 1.5 | 1.5 | 4 |
| Distilled water | 62 | 62 | |

Preparation of Suspension:

PVP, which in this case functions as a binder, is dissolved in warm water at a temperature of about 50° C. so that the PVP concentration corresponds to 10% (w/w). The remaining amount of water is then added under stirring. Calcium carbonate is then added to the mixture under stirring and the resulting mixture containing a suspension of calcium carbonate in water is sieved through a 177 microns sieve immediately before use. The resulting suspension, i.e. the feed, is manually stirred at regular intervals to ensure a homogeneous feed.

Spray Drying Parameters:

The homogeneous feed is sprayed into a NIRO SD-6.3N spray dryer using a pressure nozzle atomizer positioned at the bottom of the chamber and with the spray pointing upwards in order to obtain as large particles as possible. The following process parameters are employed:

| | |
|---|---|
| Inlet temperature: | about 280° C. |
| Outlet temperature: | about 130° C. |
| Fluidising air velocity: | 670 kg/hour |
| Nozzle pressure: | about 20 bar |

Characterisation

Examination of the pellets by SEM showed perfectly spherical pellets with a porous surface. The pellets however looked more porous than the pellets from Examples 1 and 2.

| | |
|---|---|
| Loss on drying (%): | 0.0 |
| Karl Fischer (%): | 0.5 |
| Apparent density loose/tapped (g/ml): | 0.80/0.86 |

| Malvern: | D(v, 0.5) (microns) | Span |
|---|---|---|
| 0.25 bar | 113 | 1.179 |
| 0.5 bar | 115 | 1.171 |
| 1.0 bar | 88 | 1.939 |
| 1.5 bar | 51 | 2.930 |
| 1.75 bar | 44 | 3.628 |
| 2.0 bar | 33 | 4.039 |

| | |
|---|---|
| True density (g/cm³): | 2.635 |
| Rv = | 55.7 |

EXAMPLE 4

Preparation of Calcium Carbonate Pellets with Lactose as Filler Material

| Ingredients | kg | % w/w in suspension | % w/w dry matter |
|---|---|---|---|
| Calcium Carbonate | 47.5 | 47.4 | 91.3 |
| Lactose | 2.5 | 2.5 | 4.8 |
| Pharmacoat 603 | 2.0 | 2.0 | 3.8 |
| Silicone oil antifoam SE2 | ca. 0.2 | Ca. 0.2 | |
| Distilled water | 48 | 47.9 | |

Preparation of Feed

The feed is prepared as described in Example 1.

Spray Drying Parameters

The homogeneous feed is sprayed into a NIRO S 12.5 spray dryer using a pressure nozzle atomizer positioned at the bottom of the chamber and with the spray pointing upwards in order to obtain as large particles as possible. The following process parameters are employed:

| | |
|---|---|
| Inlet temperature: | about 290° C. |
| Outlet temperature: | about 130° C. |
| Fluidising air velocity: | 1260 kg/hour |
| Feed flow: | 95 l/h |
| Nozzle pressure: | about 20 bar |

Characterisation

Visualization by SEM showed the pellets to be spherical and much like those of Examples 1 and 2.

| | |
|---|---|
| Loss on drying (%): | 0.51 |
| Apparent density loose/tapped (g/ml): | 0.72/0.79 |

| Malvern: | D(v, 0.5) (microns) | Span |
|---|---|---|
| 0.25 bar | 183 | 1.015 |
| 0.5 bar | 176 | 1.062 |
| 1.0 bar | 157 | 1.241 |
| 1.5 bar | 154 | 1.226 |
| 1.75 bar | 125 | 1.521 |
| 2.0 bar | 114 | 1.685 |

-continued

| | |
|---|---|
| True density (g/cm³): | 2.367 |
| Rv = | 12.5 |

EXAMPLE 5

Coating of Inert Calcium Hydrogen Phosphate Pellets from Example 1 with Diltiazem Hydrochloride.

1000 g of sieved (90 microns) pellets produced in Example 1 are coated with a solution of diltiazem hydrochloride in water. Pharmacoat 603 is used as a binder. The composition is shown in Table 2 below. The amount of diltiazem applied corresponds to 50% wt. of the spray-dried pellets.

TABLE 2

| Ingredients | Amount(g) | % of dry substance |
|---|---|---|
| Inert pellets | 1000 | 64.5 |
| Diltiazem hydrochloride | 500 | 32.3 |
| Pharmacoat 603 | 50 | 3.2 |
| Distilled water | 1950 | |

Preparation of Coating Solution:

Pharmacoat 603 is dissolved in water at 90° C. After cooling, diltiazem hydrochloride is dissolved in the solution.

| Coating parameters: | |
|---|---|
| Apparatus: | Fluidized bed GPCG 1/6" Wurster, Glatt GmbH, Germany |
| Nozzle position: | bottom (in order to obtain a long drying time and thereby avoiding agglomeration) |
| Nozzle diameter: | 1.0 mm |
| Inlet air temperature: | about 60-65° C. |
| Product temperature: | 36-37° C. |
| Nozzle pressure: | 2.5 bar |
| Spraying rate: | about 10 g/min |
| Fluidizing air velocity: | about 50-53 m³/hour |

The coating procedure is started immediately after the pellets have been introduced into the apparatus.

Characterisation

Visualization by SEM shows that the surface of the coated pellets is not as uniform as before coating, but still satisfactory.

| | | |
|---|---|---|
| Karl Fischer (%): | | 2.5 |
| Apparent density loose/tapped (g/ml): | | 0.79/0.93 |
| Flow rate: | 2.5 mm: | 2 min 34 sec. |
| | 5 mm: | 22 sec. |
| | 8 mm: | 7 sec. |
| Malvern: | D(v, 0.5) (microns): | 0.5 bar: 240 |
| | | 1.0 bar: 234 |
| | span | 0.5 bar: 0.63 |
| | | 1.0 bar: 0.72 |

EXAMPLE 6

Coating of Pellets of Example 5 with a Release Modifying Coating

| | Composition | |
|---|---|---|
| Ingredients | Amount(g) | % of dry substance |
| Diltiazem pellets (Ex 5) | 1000 | 33.3 |
| Surelease E-7-7050 (25% solid) | 2000 | 66.6 |
| Distilled water | 1333 | |

Preparation of Coating Solution

Surelease E-7-7050 is mixed with water and stirred for 15 minutes before use.

| Coating parameters: | |
|---|---|
| Apparatus: | Fluidized bed GPCG 1/6" Wurster, Glatt GmbH, Germany |
| Nozzle position: | bottom (in order to obtain a long drying time and thereby avoiding agglomeration) |
| Nozzle diameter: | 1.0 mm |
| Inlet air temperature: | about 50° C. |
| Product temperature: | about 32° C. |
| Nozzle pressure: | 2.5 bar |
| Spraying rate: | about 9.0 g/min |
| Fluidizing air velocity: | about 59 m³/hour |

The coating procedure is started immediately after the pellets have been introduced into the apparatus. Samples are withdrawn during the coating process after applying Surelease corresponding to 25%, 37.5% and 50% weight gain. After finishing the coating, the pellets are dried for 1 hour at 60° C.

Characterisation

Visualization by SEM showed that the Surelease coated pellets are again more uniform.

Concentration of active substance in the coated pellets:

| | | Measured | Theoretical |
|---|---|---|---|
| 1) | 25% | 247 mg/g | 258 mg/g |
| 2) | 37.5% | 229 mg/g | 235 mg/g |
| 3) | 50% | 207 mg/g | 215 mg/g |

The following results were obtained on pellets coated with 50% Surelease.

| | | |
|---|---|---|
| Apparent density: | Loose: | 0.714 g/ml |
| | Tapped: | 0.848 g/ml |
| Flow rate: | 2.5 mm: | 2 min. 43 sec. |
| | 5 mm: | 22 sec. |
| | 8 mm: | 6 sec. |
| Karl Fischer: | 1.6% | |
| Malvern: D(v, 0.5): | 293 μm | |
| Span: | 0.613 | |

Pellets coated with 50% polymer were separated into 3 size fractions for dissolution.

4) 125-200 microns
5) 200-297 microns
6) 297-420 microns

Based on the results from dissolution of the different size fractions it was found that the dissolution rate per $cm^2$ for the first 6 hours is the same no matter what size the pellets have.

EXAMPLE 7

Coating of Pellets from Example 1 with Furosemide 1000 g of sieved (90 microns) pellets prepared in Example 1 are coated with a dispersion of furosemide in water. Pharmacoat 603 is used as a binder. The composition is shown in Table 3 below. The amount of furosemide applied corresponds to 30% wt. of the uncoated pellets.

TABLE 3

| Ingredients | Amount (g) | % w/w of dry substance |
| --- | --- | --- |
| Inert pellets | 1000 | 69.0 |
| Furosemide | 300 | 20.7 |
| Pharmacoat 603 | 150 | 10.3 |
| Distilled water | 3450 | |

Preparation of Coating Solution:

Pharmacoat 603 is dissolved in water at 90° C. After cooling of the solution, furosemide is dispersed therein. The dispersion is stirred constantly during the coating procedure.

| Coating parameters: | |
| --- | --- |
| Apparatus: | Fluidized bed CPCG 1/6" |
| | Wurster, Glatt GmbH, Germany |
| Nozzle position: | bottom (in order to obtain a long drying time and thereby avoiding agglomeration) |
| Nozzle diameter: | 1.0 mm |
| Inlet air temperature: | about 53-60° C. |
| Product temperature: | 27-30° C. |
| Nozzle pressure: | 2.5 bar |
| Spraying rate: | about 12 g/min |
| Fluidizing air velocity: | about 44-67 m³/hour |

The coating procedure is started immediately after the pellets have been introduced into the apparatus. After coating, the pellets are dried at 40° C. for 1 hour.

Characterisation

The appearance of the pellets coated with furosemide is acceptable.

EXAMPLE 8

Coating of Pellets from Example 7 with a Release Modifying Coating

| | Composition | |
| --- | --- | --- |
| Ingredients | Amount (g) | % of dry substance |
| Furosemide pellets (Ex 7) | 1000 | 66.7 |
| Surelease E-7-7050 (25% solid) | 2000 | 33.3 |
| Distilled water | 1333 | |

Preparation of Coating Solution

Surelease E-7-7050 is mixed with water and stirred for 15 minutes before use.

| Coating parameters: | |
| --- | --- |
| Apparatus: | Fluidized bed GPCG 1/6" Wurster, Glatt GmbH, Germany |
| Nozzle position: | bottom (in order to obtain a long drying time and thereby avoiding agglomeration) |
| Nozzle diameter: | 1.0 mm |
| Inlet air temperature: | about 50° C. |
| Product temperature: | about 31° C. |
| Nozzle pressure: | 2.5 bar |
| Spraying rate: | about 9.0 g/min |
| Fluidizing air velocity: | about 60 m³/hour |

The coating procedure is started immediately after the pellets have been introduced into the apparatus.

Samples are withdrawn during the coating process after applying Surelease corresponding to 25%, 37.5% and 50% weight gain. After finishing the coating, the pellets are dried for 1 hour at 60° C.

Characterisation

Concentration of active substance in the coated pellets:

| | | Measured | Theoretical |
| --- | --- | --- | --- |
| 1) | 25% | 164 mg/g | 180 mg/g |
| 2) | 37.5% | 149 mg/g | 167 mg/g |
| 3) | 50% | 137 mg/g | 150 mg/g |

EXAMPLE 9

Spray Drying of inert $CaHPO_4$ Pellets—Low Binder Concentration

A suspension was prepared from the following ingredients:

| Ingredients | kg | % w/w in suspension | % w/w dry matter |
| --- | --- | --- | --- |
| Di-Cafos C 92-05 | 47.5 | 51.2 | 93.1 |
| Maltodextrin 01982 | 2.5 | 2.7 | 4.9 |
| Pharmacoat 603 | 1.0 | 1.1 | 2.0 |
| Silicone oil antifoam SE2 | ca. 0.07 | ca. 0.08 | |
| Distilled water | 41.7 | 44.9 | |

Preparation of Feed:
The feed is prepared as described in Example 1.

Spray Drying Parameters:
The homogeneous feed is sprayed into a NIRO S 12.5 spray dryer using a pressure nozzle atomizer positioned at the bottom of the chamber and with the spray pointing upwards in order to obtain as large particles as possible. The following process parameters are employed:

| | |
|---|---|
| Inlet temperature: | about 290° C. |
| Outlet temperature: | about 129° C. |
| Fluidising air velocity: | 1260 kg/hour |
| Flow rate of feed: | about 90 l/h |
| Nozzle pressure: | about 20 bar |

Characterisation of Spray Dried Pellets:

| | | | |
|---|---|---|---|
| Loss on drying (%): | | 0.40 | |
| Apparent density loose/tapped (g/ml): | | 0.94/1.00 | |
| Malvern: | D(v, 0.5) | (microns) | Span |
| | 0.25 bar | 163 | |
| | 0.5 bar | 176 | |
| | 1.0 bar | 134 | 1.505 |
| | 1.5 bar | 97 | 2.050 |

$Rv = 44.9$

EXAMPLE 10

Spray Drying of Inert CaHPO$_4$ Pellets—Low Filler Concentration

A suspension was prepared from the following ingredients:

| Ingredients | kg | % w/w in suspension | % w/w dry matter |
|---|---|---|---|
| Di-Cafos C 92-05 | 48.75 | 52.8 | 93.8 |
| Maltodextrin 01982 | 1.25 | 1.92 | 2.4 |
| Pharmacoat 603 | 2.0 | 2.2 | 3.8 |
| Silicone oil antifoam SE2 | ca. 0.08 | ca. 0.09 | |
| Distilled water | 42.3 | 45.8 | |

Preparation of Feed:
The feed is prepared as described in Example 1

Spray Drying Parameters:
The homogeneous feed is sprayed into a NIRO S 12.5 spray dryer using a pressure nozzle atomizer positioned at the bottom of the chamber and with the spray pointing upwards in order to obtain as large particles as possible. The following process parameters are employed:

| | |
|---|---|
| Inlet temperature: | about 300° C. |
| Outlet temperature: | about 129° C. |
| Fluidising air velocity: | 1260 kg/hour |
| Flow rate of feed: | about 86 l/h |
| Nozzle pressure: | about 20 bar |

Characterisation of Spray Dried Pellets:

| | | | |
|---|---|---|---|
| Loss on drying (%): | | 0.29 | |
| Apparent density loose/tapped (g/ml): | | 0.87/0.94 | |
| Malvern: | D(v, 0.5) | (microns) | Span |
| | 0.25 bar | 158 | |
| | 0.5 bar | 165 | |
| | 1 bar | 161 | 1.0 |
| | 1.5 bar | 136 | 1.5 |

$Rv = 17.6$

EXAMPLE 11

Spray Drying of Inert CaHPO$_4$ Pellets—High Binder Concentration

A suspension was prepared from the following ingredients:

| Ingredients | kg | % w/w in suspension | % w/w dry matter |
|---|---|---|---|
| Di-Cafos C 92-05 | 47.5 | 46.5 | 89.6 |
| Maltodextrin 01982 | 2.5 | 2.4 | 4.7 |
| Pharmacoat 603 | 3.0 | 2.9 | 5.7 |
| Silicone oil antifoam SE2 | ca. 0.19 | ca. 0.19 | |
| Distilled water | 48.9 | 47.9 | |

Preparation of Feed:
The feed is prepared as described in Example 1

Spray Drying Parameters:

| | |
|---|---|
| Inlet temperature: | 320° C. |
| Outlet temperature: | 129° C. |
| Fluidising air velocity: | 1260 kg/hour |
| Nozzle pressure: | about 20 bar |

Characterisation of Spray Dried Pellets:

| | | | |
|---|---|---|---|
| Loss on drying (%): | | 0.72 | |
| Aparent density loose/tapped (g/ml): | | 0.81/0.92 | |
| Malvern: | D(v, 0.5) | (microns) | Span |
| | 0.25 bar | 192 | 0.9979 |
| | 0.5 bar | 188 | 1.029 |
| | 1 bar | 189 | 1.106 |
| | 1.5 bar | 178 | 1.103 |
| | 1.75 bar | 160 | 1.289 |
| | 2.0 bar | 146 | 1.448 |

$Rv = 5.3$

EXAMPLE 12

Spray Drying of Inert CaHPO$_4$ Pellets—High Filler Concentration

A suspension was prepared from the following ingredients:

| Ingredients | kg | % w/w in suspension | % w/w dry matter |
|---|---|---|---|
| Di-Cafos C 92-05 | 30 | 38.3 | 76.9 |
| Maltodextrin 01982 | 7.6 | 9.7 | 19.2 |
| Pharmacoat 603 | 1.5 | 1.9 | 3.8 |
| Silicone oil antifoam SE2 | ca. 0.32 | ca. 0.2 | |
| Distilled water | 39.1 | 49.9 | |

Preparation of Feed:
The feed is prepared as described in Example 1.

Spray Drying Parameters:
The homogeneous feed is spray dried using a NIRO SD-12.5 spray dryer using a pressure nozzle atomizer (1.1 SD) positioned at the bottom of the chamber and with the spray pointing upwards in order to obtain as large particles as possible. The following process parameters are employed:

| | |
|---|---|
| Inlet temperature: | about 302° C. |
| Outlet temperature: | about 130° C. |
| Fluidising air velocity: | 1260 kg/hour |
| Flow rate of feed: | about 94 l/h |
| Nozzle pressure: | 20 bar |

Characterisation of Spray Dried Pellets:

| | | | |
|---|---|---|---|
| Residual water (%): | | | 1.46% |
| Apparent density loose/tapped (g/ml): | | | 0.79/0.88 |
| Malvern: | D(v, 0.5) | (microns) | Span |
| | 0.25 bar | 172 | 1.033 |
| | 0.5 bar | 175 | 1.007 |
| | 1 bar | 158 | 1.150 |
| | 1.5 bar | 131 | 1.502 |
| Density (Hg) (g/ml) (sieve fraction 125-180 μm): | | | 1.283 |
| True density (g/cm$^3$): | | | 2.3989 |
| Rv = | | | 25.1 |

EXAMPLE 13

Spray Drying of Inert CaHPO$_4$ Pellets—High Filler Content

A suspension was prepared from the following ingredients:

| Ingredients | kg | % w/w in suspension | % w/w dry matter |
|---|---|---|---|
| Di-Cafos C 92-05 | 31.5 | 40.1 | 80.8 |
| Maltodextrin 01982 | 6.1 | 7.8 | 15.4 |
| Pharmacoat 603 | 1.5 | 1.9 | 3.8 |
| Silicone oil antifoam SE2 | ca. 0.269 | ca. 0.3 | |
| Distilled water | 39.1 | 49.8 | |

Preparation of Feed:
The feed is prepared as described in Example 1.

Spray Drying Parameters:
The homogeneous feed is spray dried using a NIRO SD-12.5 spray dryer using a pressure nozzle atomizer (1.1 SD) positioned at the bottom of the chamber and with the spray pointing upwards in order to obtain as large particles as possible. The following process parameters are emplyed:

| | |
|---|---|
| Inlet temperature: | about 290° C. |
| Outlet temperature: | about 130° C. |
| Fluidising air velocity: | 1260 kg/hour |
| Flow rate of feed: | about 96 l/h |
| Nozzle pressure: | about 20 bar |

Characterisation of Spray Dried Pellets:

| | | | |
|---|---|---|---|
| Residual water (%): | | | 0.85% |
| Apparent density loose/tapped (g/ml): | | | 0.77/0.91 |
| Malvern: | D(v, 0.5) | (microns) | Span |
| | 0.25 bar | 176 | 0.9311 |
| | 0.5 bar | 175 | 0.9073 |
| | 1 bar | 159 | 1.123 |
| | 1.5 bar | 133 | 1.449 |
| Density (Hg) (g/ml) (sieve fraction 125-180 μm): | | | 1.378 |
| True density (g/cm$^3$): | | | 2.5327 |
| Rv = | | | 24.0 |

EXAMPLE 14

Spray Drying of Inert CaHPO$_4$ Pellets—High Filler Content

A suspension was prepared from the following ingredients:

| Ingredients | kg | % w/w in suspension | % w/w dry matter |
|---|---|---|---|
| Di-Cafos C 92-05 | 30 | 38.3 | 76.9 |
| Lactose | 7.6 | 9.7 | 19.2 |
| Pharmacoat 603 | 1.5 | 1.9 | 3.8 |
| Silicone oil antifoam SE2 | ca. 0.2 | ca. 0.3 | |
| Distilled water | 39.1 | 49.9 | |

Preparation of Feed:
The feed is prepared as described in Example 1.

Spray Drying Parameters:
The homogeneous feed is spray dried using a NIRO SD-12.5 spray dryer using a pressure nozzle atomizer (1.1

SD) positioned at the bottom of the chamber and with the spray pointing upwards in order to obtain as large particles as possible. The following process parameters are employed:

| | |
|---|---|
| Inlet temperature: | about 245° C. |
| Outlet temperature: | about 130° C. |
| Fluidising air velocity: | 1260 kg/hour |
| Flow rate of feed: | about 86 l/h |
| Nozzle pressure: | 20 bar |

Characterisation of Stray Dried Pellets:

| | | | |
|---|---|---|---|
| Residual water (%): | | | 1.13 |
| Aapparent density loose/tapped (g/ml): | | | 0.77/0.91 |
| Malvern: | D(v, 0.5) | (microns) | Span |
| | 0.25 bar | 173 | 0.9899 |
| | 0.5 bar | 162 | 1.096 |
| | 1 bar | 145 | 1.277 |
| | 1.5 bar | 115 | 1.606 |
| Density (Hg) (g/ml) (sieve fraction 125-180 μm): | | | 1.459 |
| True density (g/cm$^3$) | | | 2.4383 |
| Rv = | | | 29.0 |

EXAMPLE 15

Spray Drying of Inert CaHPO$_4$ Pellets—High Filler Content

A suspension was prepared from the following ingredients:

| Ingredients | kg | % w/w in suspension | % w/w dry matter |
|---|---|---|---|
| Di-Cafos C 92-05 | 31.5 | 340.1 | 80.8 |
| Lactose | 6.1 | 7.8 | 15.4 |
| Pharmacoat 603 | 1.5 | 1.9 | 3.8 |
| Silicone oil antifoam SE2 | ca. 0.314 | ca. 0.4 | |
| Distilled water | 39.1 | 49.8 | |

Preparation of Feed:

The feed is prepared as described in Example 1.

Spray Drying Parameters:

The homogeneous feed is spray dried using a NIRO SD-12.5 spray dryer using a pressure nozzle atomizer (1.1 SD) positioned at the bottom of the hamber and with the spray pointing upwards in order to obtain as large particles as possible. The following process parameters are employed:

| | |
|---|---|
| Inlet temperature: | about 249° C. |
| Outlet temperature: | about 120° C. |
| Fluidising air velocity: | 1260 kg/hour |
| Flow rate of feed: | about 86 l/h |
| Nozzle pressure: | 20 bar |

Characterisation of Spray Dried Pellets:

| | | | |
|---|---|---|---|
| Residual water (%): | | | |
| Apparent density loose/tapped (g/ml): | | | 0.83/1.0 |
| Malvern: | D(v, 0.5) | (microns) | Span |
| | 0.25 bar | 160 | 1.006 |
| | 0.5 bar | 157 | 1.052 |
| | 1 bar | 146 | 1.249 |
| | 1.5 bar | 131 | 1.385 |
| Density (Hg) (g/ml) (sieve fraction 125-180 μm): | | | 1.585 |
| True density (g/cm$^3$) | | | 2.5768 |
| Rv = | | | 16.6 |

EXAMPLE 16—COMPARATIVE

Spray Drying of Inert CaHPO$_4$ Pellets—No Filler, PVP as Binder

A suspension was prepared from the following ingredients:

| Ingredients | kg | % w/w in suspension | % w/w dry matter |
|---|---|---|---|
| Di-Cafos C 92-05 | 50.0 | 48.1 | 96.2 |
| PVP | 2.0 | 1.9 | 3.8 |
| Distilled water | 52 | 50 | |

Preparation of Feed:

The feed is prepared as described in Example 1.

Spray Drying Parameters:

The homogeneous feed is spray dried using a NIRO SD-12.5 spray dryer using a pressure nozzle atomizer (1.1 SD) positioned at the bottom of the chamber and with the spray pointing upwards in order to obtain as large particles as possible. The following process parameters are employed:

| | |
|---|---|
| Inlet temperature: | about 237° C. |
| Outlet temperature: | about 120° C. |
| Fuidising air velocity: | 1260 kg/hour |
| Flow rate of feed: | about 74 l/h |
| Nozzle pressure: | about 20 bar |

Characterisation of Spray Dried Pellets:

| | | | |
|---|---|---|---|
| Residual water (%): | | | 0.45 |
| Apparent density loose/tapped (g/ml): | | | 0.86/1.0 |
| Malvern: | D(v, 0.5) | (microns) | Span |
| | 0.25 bar | 136 | 0.8919 |
| | 0.5 bar | 123 | 1.236 |
| | 1 bar | 53 | 2.476 |
| | 1.5 bar | 38 | 2.879 |
| Density (Hg) (g/ml) (not sieve): | | | 1.7495 |
| Rv = | | | 69.1 |

EXAMPLE 17—COMPARATIVE

Spray Drying of Inert CaHPO$_4$ Pellets—No Filler, High PVP

A suspension was prepared from the following ingredients:

| Ingredients | kg | % w/w in suspension | % w/w dry matter |
|---|---|---|---|
| Di-Cafos C 92-05 | 50.0 | 47.2 | 94.3 |
| PVP | 3.0 | 2.8 | 5.7 |
| Distilled water | 53 | 50 | |

Preparation of Feed:
The feed is prepared as described in Example 1.

Spray Drying Parameters:
The homogeneous feed is spray dried using a NIRO SD-12.5 spray dryer using a pressure nozzle atomizer (1.1 SD) positioned at the bottom of the chamber and with the spray pointing upwards in order to obtain as large particles as possible. The following process parameters are employed:

| | |
|---|---|
| Inlet temperature: | about 290° C. |
| Outlet temperature: | about 130° C. |
| Fluidising air velocity: | 1260 kg/hour |
| Flow rate of feed: | about 75 l/h |
| Nozzle pressure: | about 20 bar |

Characterisation of Spray Dried Pellets:

| | | | |
|---|---|---|---|
| Residual water (%): | | | 0.21 |
| Apparent density loose/tapped (g/ml): | | | 0.93/1.11 |
| Malvern: | D(v, 0.5) | (microns) | Span |
| | 0.25 bar | 141 | 0.838 |
| | 0.5 bar | 138 | 0.892 |
| | 1 bar | 113 | 1.398 |
| | 1.5 bar | 76 | 1.962 |
| Density (Hg) (g/ml) (sieve fraction 125-180 μm): | | | 1.773 |
| True density (g/cm$^3$): | | | 2.8165 |
| Rv = | | | 44.9 |

EXAMPLE 18

Spray Drying of Inert CaHPO$_4$ Pellets—No Filler

A suspension was prepared from the following ingredients:

| Ingredients | kg | % w/w in suspension | % w/w dry matter |
|---|---|---|---|
| Di-Cafos C 92-05 | 100 | 53.8 | 96.2 |
| Pharmacoat 603 | 4 | 2.2 | 3.8 |
| Silicone oil antifoam SE2 | ca. 0.063 | ca. 0.03 | |
| Distilled water | 81.7 | 44.0 | |

Preparation of Feed:
The feed is prepared as described in Example 1.

Spray Drying Parameters:
The homogeneous feed is spray dried using a NIRO SD-12.5 spray dryer using a pressure nozzle atomizer (1.1 SD) positioned at the bottom of the chamber and with the spray pointing upwards in order to obtain as large particles as possible. The following process parameters are employed:

| | |
|---|---|
| Inlet temperature: | about 295° C. |
| Outlet temperature: | about 120° C. |
| Fluidising air velocity: | 1260 kg/hour |
| Flow rate of feed: | about 94 l/h |
| Nozzle pressure: | about 20 bar |

Characterisation of Spray Dried Pellets:

| | | | |
|---|---|---|---|
| Residual water (%): | | | 0.29 |
| Apparent density loose/tapped (g/ml): | | | 0.87/0.92 |
| Malvern: | D(v, 0.5) | (microns) | Span |
| | 0.25 bar | 171 | 0.9461 |
| | 0.5 bar | 169 | 0.8626 |
| | 1 bar | 167 | 0.9362 |
| | 1.5 bar | 157 | 1.150 |
| Density (Hg) (g/ml) (sieve fraction 125-180 μm): | | | 1.636 |
| True density (g/cm$^3$): | | | 3.081 |
| Rv = | | | 7.1 |

The invention claimed is:

1. A process for the production of drug carrier pellets comprising spray-drying a solution of a physiologically tolerable cellulosic binder, containing a physiologically tolerable inert particulate carrier having a particulate size D(v. 0.5) of less than 50 μm, and a filler selected from lactose, lactose monohydrate, sucrose, fructose, a fructooligosaccharide, inulin, mannitol, sorbitol, xylitol, inositol, isomalt or maltodextrin.

2. A process as claimed in claim 1 wherein said solution further contains an active drug substance.

3. A process as claimed in claim 1 or claim 2 wherein said carrier pellets are impregnated and/or coated one or more times.

4. A process as claimed in claim 3 wherein said carrier pellets are impregnated and/or coated with an active drug substance.

5. A process as claimed in claim 4 wherein said impregnated and/or coated pellets are further coated.

6. A process as claimed in claim 5 wherein said further coating is a release modifying coating.

7. A process as claimed in any one of claims 4 to 6 wherein said coatings are applied by fluidized bed coating.

8. A spray-dried pellet comprising a physiologically tolerable cellulosic binder, a physiologically tolerable inert particulate carrier having a particle size D(v, 0.5) of less than 50 μm and a filler selected from lactose, lactose monohydrate, sucrose, fructose, fructooligosaecharides, inulin, mannitol, sorbitol, xylitol, inositol, isomalt and maltodextrin.

9. The pellet of claim 8 wherein said cellulosic binder is a cellulose or cellulose derivative which is at least partially soluble in solvent or solvent mixture used for spray drying.

10. The pellet of claim 9 wherein said cellulosic binder is an alkylcellulose, a hydroxyalkylalkylcellulose, a hydroxyalkylcellulose or a carboxyalkylcellulose.

11. The pellet of claim 10 wherein said cellulosic binder is selected from methylcellulose, ethylcellulose, hydroxypropylmethylcellulose, hydroxyethylmethylcellulose, hydroxypropylcellulose and sodium carboxymethylcellulose.

12. The pellet of claim 8 wherein said cellulosic binder constitutes from 0.5-15% wt of said spray-dried pellets.

13. The pellet of claim 8 wherein said inert particulate carrier is a polymer, a clay or an inorganic carbonate, silicate, sulphate, phosphate or oxide.

14. The pellet of claim 13 wherein said inert particulate carrier is selected from activated carbon, kaolin, calcium carbonate, calcium silicate, calcium magnesium silicate, calcium lactate, calcium gluconate, calcium glycerophosphate, calcium phosphate, calcium hydrogen phosphate, calcium glucuronute, calcium aspartate, calcium glucoheptanoate, sodium hydrogen carbonate, sodium sulphate, magnesium sulphate, magnesium carbonate, barium carbonate, barium sulphate, and hydroxyapatites.

15. The pellet of claim 8 wherein said spray dried pellets further comprise at least one of an anti-foaming agent, and an active drug substance, or a mixture of two or more thereof.

16. The pellet of claim 15 having said active drug substance contained or, impregnated therein or coated thereon.

17. The pellet of claim 8 further coated with a release modifying coating.

18. The pellet of claim 8 having a D(v, 0.5) of 25 to 500 µm and a span value of no greater than 2.5.

19. The pellet of claim 8 having a robustness value (Rv) of no more than 40.

20. A pharmaceutical composition comprising a spray-dried pellet as claimed in claim 8 containing, impregnated with or coated with an active drug substance and optionally further comprising at least one pharmaceutically acceptable carrier or excipient.

21. A composition as claimed in claim 20 in tablet, coated tablet or capsule form.

* * * * *